US 6,602,678 B2

(12) United States Patent
Kwon et al.

(10) Patent No.: US 6,602,678 B2
(45) Date of Patent: *Aug. 5, 2003

(54) NON- OR MINIMALLY INVASIVE MONITORING METHODS (75) Inventors: Sung Yun Kwon, Fremont, CA (US); Terry L. Burkoth, Palo Alto, CA (US)

(73) Assignee: PowderJect Research Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/022,633

(22) Filed: Dec. 17, 2001

(65) Prior Publication Data

US 2002/0102625 A1 Aug. 1, 2002

Related U.S. Application Data (63) Continuation-in-part of application No. 09/803,828, filed on Mar. 12, 2001, now Pat. No. 6,482,604, which is a continuation of application No. 09/390,068, filed on Sep. 3, 1999, now Pat. No. 6,207,400.
(60) Provisional application No. 60/099,157, filed on Sep. 4, 1998.

(51) Int. Cl.[7] .............................. C12Q 1/54; C12Q 1/00; C12Q 1/26
(52) U.S. Cl. ..................... 435/14; 435/4; 435/283.1; 435/25
(58) Field of Search ..................... 435/14, 4, 283.1, 435/25

(56) References Cited

U.S. PATENT DOCUMENTS

| 4,344,438 | A | 8/1982 | Schultz ..................... 128/634 |
| 4,401,122 | A | 8/1983 | Clark, Jr. ................... 128/635 |
| 4,945,050 | A | 7/1990 | Sanford et al. ........... 435/172.1 |
| 5,036,861 | A | 8/1991 | Sembrowich et al. ....... 128/763 |
| 5,076,273 | A | 12/1991 | Schoendorfer et al. ..... 128/632 |
| 5,101,814 | A | 4/1992 | Palti .......................... 128/635 |
| 5,139,023 | A | 8/1992 | Stanley et al. .............. 128/637 |
| 5,140,985 | A | 8/1992 | Schroeder et al. .......... 128/632 |
| 5,149,655 | A | 9/1992 | McCabe ..................... 435/287 |
| 5,204,253 | A | 4/1993 | Sanford ................... 435/172.3 |
| 5,279,543 | A | 1/1994 | Glickfeld et al. ............. 604/20 |
| 5,342,789 | A | 8/1994 | Chick et al. ................. 436/501 |
| 5,362,307 | A | 11/1994 | Guy et al. ..................... 604/20 |
| 5,445,611 | A | 8/1995 | Eppstein et al. .............. 604/49 |
| 5,458,140 | A | 10/1995 | Eppstein et al. ............ 128/632 |
| 5,628,310 | A | 5/1997 | Rao et al. ................... 128/632 |
| 5,636,632 | A | 6/1997 | Bommannan et al. ...... 128/632 |
| 5,722,397 | A | 3/1998 | Eppstein ..................... 128/633 |
| 5,730,714 | A | 3/1998 | Guy et al. ..................... 604/20 |
| 5,735,273 | A | 4/1998 | Kurnik et al. .............. 128/635 |
| 5,771,890 | A | 6/1998 | Tamada ...................... 128/635 |
| 5,827,183 | A | 10/1998 | Kurnik et al. .............. 600/345 |
| 5,853,751 | A | 12/1998 | Masiv ........................ 424/449 |

(List continued on next page.)

FOREIGN PATENT DOCUMENTS

| WO | WO 94/24263 | 10/1994 |
| WO | WO 96/00110 | 1/1996 |
| WO | WO 96/04947 | 2/1996 |
| WO | WO 96/12513 | 5/1996 |
| WO | WO 96/20022 | 7/1996 |
| WO | WO 97/09970 | 3/1997 |

*Primary Examiner*—Louise N. Leary
(74) *Attorney, Agent, or Firm*—Thomas P. McCracken (57) ABSTRACT

An apparatus for sensing an analyte is described, wherein the apparatus includes an interface contact element that is used to establish an interface with a quantity of body fluid. The interface contact element is adapted to facilitate diffusion of a target analyte across the interface essentially free of net mass fluid transport. The quantity of body fluid is exposed to the interface contact element through micropathways. The apparatus can also include a sensing material adapted to sense the target analyte with at least one analytical method. Methods for using the apparatus in a non- or minimally invasive monitoring technique are also described.

28 Claims, 2 Drawing Sheets

U.S. PATENT DOCUMENTS

| | | | |
|---|---|---|---|
| 5,885,211 A | 3/1999 | Eppstein et al. | 600/309 |
| 5,902,603 A | 5/1999 | Chen et al. | 424/449 |
| 5,954,685 A | 9/1999 | Tierney | 604/20 |
| 6,022,316 A | 2/2000 | Eppstein et al. | 606/167 |
| 6,030,399 A | 2/2000 | Ignotz et al. | 436/501 |
| 6,040,194 A | 3/2000 | Chick et al. | 600/345 |
| 6,091,975 A | 7/2000 | Daddona et al. | 156/73.1 |
| 6,103,033 A | 8/2000 | Say et al. | 205/777.5 |
| 6,120,676 A | 9/2000 | Heller et al. | 600/345 |
| 6,141,573 A | 10/2000 | Kurnik et al. | 600/309 |
| 6,142,939 A | 11/2000 | Eppstein et al. | 600/347 |
| 6,144,869 A | 11/2000 | Berner et al. | 600/345 |
| 6,175,752 B1 | 1/2001 | Say et al. | 435/14 |
| 6,207,400 B1 * | 3/2001 | Kwon | 435/14 |
| 6,482,604 B2 | 11/2002 | Kwon | 435/14 |

* cited by examiner

NON- OR MINIMALLY INVASIVE MONITORING METHODS

CROSS-REFERENCE TO RELATED APPLICATIONS

This is a continuation-in-part of U.S. application Ser. No. 09/803,828, filed Mar. 12, 2001, now U.S. Pat. No. 6,482,604, which is a continuation of U.S. application Ser. No. 09/390,068, filed Sep. 3, 1999, now U.S. Pat. No. 6,207,400, which claimed the benefit of U.S. provisional application Serial No. 60/099,157, filed Sep. 4, 1998, from which applications priority is claimed pursuant to 35 U.S.C. §§119(e)(1) and 120 and which applications are incorporated herein by reference in their entireties.

FIELD OF THE INVENTION

The present invention relates to methods of continuous or rapid intermittent monitoring of body fluid for the presence and/or concentration of target analytes. More particularly, the invention relates to using diffusion of a target analyte from a body fluid such as interstitial fluid via a micro-pathway, and an interface contact element that is used to establish an equilibrium of analyte concentration between the body fluid and the interface contact element. The concentration of the target analyte can then be measured using a sensing material, thereby providing for continuous analyte monitoring such as continuous glucose monitoring by diabetic or hypoglycemic subjects.

BACKGROUND OF THE INVENTION

A number of tests are routinely performed on humans to evaluate the amount or existence of substances present in blood or other body fluids. These tests typically rely on physiological fluid samples removed from a subject, either using a syringe or by pricking the skin. One particular test entails self-monitoring of blood glucose levels by diabetics.

Diabetes is a major health concern, and treatment of the more severe form of the condition, Type I (insulin-dependent) diabetes, requires one or more insulin injections per day. Insulin controls utilization of glucose or sugar in the blood and prevents hyperglycemia that, if left uncorrected, can lead to ketosis. On the other hand, improper administration of insulin therapy can result in hypoglycemic episodes, which can result in coma and death. Hyperglycemia in diabetics has been shown to have a number of adverse long-term effects, such as heart disease, peripheral neuropathies, atherosclerosis, blindness, stroke, hypertension and kidney failure.

The value of frequent monitoring of blood glucose as a means to avoid or at least minimize the complications of Type I diabetes is well established. According to the National Institutes of Health, glucose monitoring is recommended 4–6 times a day. Patients with Type II (non-insulin-dependent) diabetes can also benefit from blood glucose monitoring in the control of their condition by way of diet, exercise, and certain oral medications.

Conventional blood glucose monitoring methods generally require the drawing of a sample of whole blood (e.g., by finger prick) for each test, and a determination of the glucose level using an analytical instrument that reads glucose concentrations by electrochemical or colorimetric methods. Type I diabetics must obtain several finger prick blood glucose measurements each day in order to maintain precise glycemic control. However, the pain and inconvenience associated with this blood sampling, has lead to poor patient compliance, despite strong evidence that precise-maintained control dramatically reduces long-term diabetic complications. In fact, these considerations can often lead to an abatement of the monitoring process by the diabetic.

Alternatives to conventional blood glucose monitoring methods that require the drawing of capillary blood sample would include methods that assess glucose in interstitial fluid. As with whole blood sampling, interstitial fluid measurement also typically requires collecting a predetermined volume of fluid sample to perform each intermittent measurement. This can be accomplished by shallow skin-pricking with a micro-needle or lancet, by laser, electroporation, skin ablation with heated elements or the like to avoid causing bleeding. Such techniques typically require application of pressure or vacuum to express an interstitial fluid sample. Interstitial fluid can be sampled through intact skin by means of electrophoretic techniques or by means of permeation enhancers. Due to the low volume of interstitial fluid in the tissue, expression of a sample through pierced skin can give inaccurate results depending upon the sample size required and the amount of trauma to the tissue from the collection procedure. Moreover, such methods cannot provide a continuous or even "real-time" monitoring of the glucose concentration in the interstitial fluid because of the time involved to access sufficient interstitial fluid to provide a measurable amount of glucose.

SUMMARY OF THE INVENTION

The present invention provides an apparatus and method for continuous or rapid intermittent monitoring of the concentration of a target analyte in a body fluid essentially without net mass fluid transport. This is achieved by diffusion of the target analyte between the body fluid and an interface contact element. The body fluid is exposed via micro-pathways that allow the body fluid to interface with the interface contact element. A portal generator, such as a particle injection device, is used to create such micro-pathways. A sensor (e.g., a hydrogel), comprising the interface contact element and a sensing material, can be incorporated into a patch that sits on the subject's skin. The patch can be configured to connect to a detector that provides quantitative results, such as by capturing an electrical signal. An instrument comprises the sensor and detector. Diffusion allows for an analytical measurement of concentration on a continuous or intermittent basis as the concentration gradient between the body fluid and interface contact element approaches continuous equilibrium. The access realized from this method allows much more frequent sampling and yields a more accurate result than existing interstitial fluid technology, and a painless measurement as opposed to the pain involved in whole blood sampling.

More particularly, the invention comprises an apparatus and method for continuous or intermittent monitoring of the concentration of a target analyte in a body fluid essentially without net mass fluid transport using diffusion of the target analyte and/or any byproducts of measurement from the body fluid to the interface contact element and vice versa. Such diffusion allows for analytical measurement of concentration on a continuous or intermittent basis as the concentration gradient between the body fluid and interface contact element approaches continuous equilibrium, and as the concentration shifts between different equilibria. The sensing material can comprise an enzyme, lectin, antibody or antibody fragment or, alternatively, a selectively reacting or binding bio-molecule or imprinted polymer to detect the presence and/or concentration of the target analyte by various analytical methods including electrochemical, (e.g., amperometric or coulometric), direct or reflective spectroscopic (e.g., absorbance, direct fluorescence, fluorescence quenching, chemiluminescence, and the like), as well as other methods.

A detector which receives the results of the analytical method can be incorporated into an instrument to detect the target analyte concentration intermittently on a cyclical basis or when triggered by the user. Such a cycle of intermittent measurement can be sufficiently short to approach continuous measurement of the target analyte concentration. The target analyte can comprise any substance significant for medical or forensic measurements including, but not limited to, nucleic acids; proteins; carbohydrates; lipids; electrolytes; drugs (e.g., anticonvulsant drugs, antipsychotic drugs, alcohol, cocaine, cannabinoids, opiates, stimulants, depressants, and/or their metabolites); gases; compounds; elements; ions; anabolic, catabolic or reproductive hormones; hormone analogs; conjugates or degradation products.

The interface contact element can be positioned on the exterior surface of the skin, the stratum corneum. The interface contact element provides a bridge between the sensing material of the sensor and the micro-pathways containing the body fluid. This interface can be facilitated by exposing the body fluid to the exterior surface of the stratum corneum by means of shallow incision, thermal ablation, tape stripping, puncturing, or lancing. In one embodiment, micro-pathways can be provided by accelerating inert, instantly dissolvable or longer-lived porous particles to a momentum sufficient to ballistically penetrate the stratum corneum reaching the viable epidermis thus forming the portal.

It is to be understood that both the foregoing general description and the following detailed description are exemplary and explanatory only and are not restrictive of the invention, as claimed.

The accompanying drawings, which are incorporated in and constitute a part of this specification, illustrate an embodiment of the invention and together with the description, serve to explain the principles of the invention and together with the description, serve to explain the principles of the invention.

DESCRIPTION OF THE EMBODIMENTS

All publications, patents, and patent applications cited herein, whether supra or infra, are hereby incorporated by reference in their entirety.

It is noted that, as used in this specification and the appended claims, the singular forms "a," "an," and "the" include plural referents unless the content clearly dictated otherwise. Thus for example, reference to "an analyte" includes mixtures of two or more analytes.

A. General Methods

A method for detecting analytes present in a body fluid present beneath the skin surface of an individual comprises two general steps, an access step and a determination step. The access step can be generalized as follows. Micro-pathways are created to provide access to the body fluid. These micro-pathways may be created using any suitable technique, for example by accelerating small particles into and/or across a skin surface. Acceleration and penetration of these particles is sufficient to create the micro-pathways that allow a quantity of body fluid of interest to flow, exude or otherwise be made accessible from beneath the skin to the skin surface. The skin surface affected by the particles generally has an overall area ranging from 0.1 to 5 $cm^2$.

The particles typically comprise an inert material. The material may be dissolvable such as commonly employed physiologically acceptable soluble materials including certain sugars or their derivatives (e.g., mannitol, sucrose, lactose, lactic acid, trehalose, and the like) and soluble or dissolvable polymers, including but not limited to polyethylene glycol (e.g., PEG 8000). Alternatively, the particles can comprise insoluble materials such as starch, $TiO_2$, calcium carbonate, phosphate salts, hydroxy apatite, porous swellable materials such as agarose, or even synthetic polymers or metals such as gold, platinum or tungsten. Insoluble materials are sloughed off with the normal skin renewal process.

If desired, the particles can be coated with or contain a locally active agent which facilitates the access step. For example, the particles can be coated with a pharmacological agent such as a vasoactive agent or an anti-inflammatory agent. The vasoactive agent is generally used to provide short-acting vasoactivity in order to optimize fluid access (i.e., to maximize the diffusional access to analytes), whereas the anti-inflammatory agent is generally used to provide local anti-inflammatory action to protect the skin. The particles can also be coated with an osmotically active agent to facilitate the access process.

The particles can be delivered using a particle injection device such as the needleless syringe systems described in commonly owned International Publication Nos. WO 94/24263, WO 96/04947, WO 96/12513, and WO 96/20022. Delivery of particles from these needleless syringe systems is generally practiced with particles having an approximate size generally ranging from 0.1 to 250 μm, or ranging from 10–70 μm. Particles larger than 250 μm can also be delivered from the devices, with the upper limitation being the point at which the size of the particles would cause untoward pain and/or damage to the skin.

The actual distance which the delivered particles will penetrate a target skin surface depends upon particle size (e.g., the nominal particle diameter assuming a roughly spherical particle geometry), particle density, the initial velocity at which the particle impacts the surface, and the density and kinematic viscosity of the skin. In this regard, optimal particle densities for use in a particle injection method generally range between 0.1 and 25 $g/cm^3$, preferably between 0.9 and 1.5 $g/cm^3$, and injection velocities generally range between 100 and 3,000 m/sec. With appropriate gas pressure, particles having an average diameter of 10–70 μm can be readily accelerated to velocities approaching the supersonic speeds of a driving gas flow. The pressure used when accelerating the particles can be less than 30 bar, preferably less than 25 bar or 20 bar or less.

Alternatively, the particles can be delivered from a "gene-gun" style particle injection device that delivers small, dense particles using either a gaseous or electric discharge. An example of a gaseous discharge device is described in U.S. Pat. No. 5,204,253. An explosive-type device is described in U.S. Pat. No. 4,945,050. One example of a helium discharge-type particle acceleration apparatus is the PowderJect® XR instrument (PowderJect Vaccines, Inc., Madison, Wis.), which instrument is described in U.S. Pat. No. 5,120,657. An electric discharge apparatus suitable for use herein is described in U.S. Pat. No. 5,149,655. The disclosure of all of these patents is incorporated herein by reference.

After the particles have been delivered into the skin, a body fluid sample is exposed to the skin surface. Typically this is a sample of, or containing, interstitial fluid. Passage of the fluid sample to the surface may be substantially instantaneous, or may occur over a period of time. The quantity of body fluid that is released to the skin surface may be varied by altering conditions such as the size and/or density of particles and the settings of the apparatus used to delivery the particles. The quantity of body fluid released may often be small, such as <1 μl that is generally sufficient for detection of the analyte.

Once the body fluid has been exposed to the skin surface (e.g., has passed to the skin surface), the presence and/or amount or concentration of the analyte in the body fluid can be determined. The body fluid can be contacted with a sensor. This detection step can, of course, be carried out in a continual or continuous manner. Continual or continuous detection allows for monitoring of target analyte concentration fluctuations. The sensor may comprise or be used in conjunction with an interface contact element that can comprise a hydrogel. Suitable gelling agents for forming a hydrogel include carbopol, calcium lactate, cellulose gum, klucel (HPMC), natrosol, gelatin powder or sodium alginate. The gelling agents can be present in water at levels such as from 1–5% by weight in water.

The interface contact element may be applied to the skin surface and sufficient time allowed for analyte from the body fluid to equilibrate in the interface contact element prior to the detection step. The time may be quite short such as from 30 seconds to 5 minutes. Detection may then be carried out by applying the sensing material to the interface contact element such as by contacting a membrane containing a suitable enzyme system for the analyte with the hydrogel.

The determination step can be generalized as follows. An initial step can entail obtaining a raw signal from a detector, which signal can be related to a target analyte present in the body fluid. The raw signal can then be used directly to obtain an answer about the analyte, for example a yes or no answer relating to the presence of the analyte, or a direct measurement indicative of the amount or concentration of the analyte. The raw signal can also be used indirectly to obtain information about the analyte. For example, the raw signal can be subjected to signal processing steps in order to correlate a measurement of the analyte in the body fluid with the concentration of that analyte in the body. Such correlation methodologies are well known to those skilled in the art.

Detection may be carried out by any suitable method that allows for detection of the target analyte. The analysis may be physical, chemical, biochemical, electrochemical, photochemical, spectrophotometric, polarimetric, colormetric or radiometric analysis.

In order to facilitate detection of the analyte, an enzyme may be disposed in the interface contact element that is contacted with the body fluid containing the analyte. Such enzymes can be capable of catalyzing a specific reaction with the target analyte (e.g., glucose) to the extent that a product of the reaction can be sensed (e.g., detected electrochemically from the generation of a current which current is detectable and proportional to the amount of the analyte which is reacted). A suitable biosensor enzyme is glucose oxidase that oxidizes glucose to gluconic acid and hydrogen peroxide. The subsequent detection of hydrogen peroxide on an appropriate electrode generates two electrons per hydrogen peroxide molecule that create a current which can be detected and related to the amount of glucose in contact with the device. Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

A number of other analyte-specific enzyme systems can be used in the methods of the invention. For example, when using a common biosensor electrode that detects hydrogen peroxide, suitable enzyme systems can be used to detect ethanol (an alcohol oxidase enzyme system), or similarly uric acid (a urate oxidase system), cholesterol (a cholesterol oxidase system), and theophylline (a xanthine oxidase system). Hydrogels containing these analyte-specific enzyme systems can be prepared using readily available techniques familiar to the ordinarily skilled artisan.

An embodiment of the sensor can be a patch that comprises an enzyme or other specific reagent that reacts with the target analyte to produce a detectable color change or other chemical signal. The color change can be assessed by comparison against a standard to determine analyte amount, or the color change can be detected using standard electronic reflectance measurement instruments. One such system is the glucose monitoring system available from Technical Chemicals and Products, Inc (TCPI) of Pompano Beach, Fla. Another suitable system is described in U.S. Pat. No. 5,267,152 to Yang et al. (a device and method for measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al. U.S. Pat. No. 5,139,023 to Stanley describes a blood glucose monitoring apparatus that relies on a permeability enhancer (e.g., a bile salt) to facilitate transdermal movement of glucose along a concentration gradient established between interstitial fluid and a receiving medium. U.S. Pat. No. 5,036,861 to Sembrowich describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder. Detection of extracted glucose is carried out using standard chemical (e.g., enzymatic) colormetric or spectrometric techniques.

Alternatively, an iontophoretic transdermal system can be used in conjunction with the sensor and the instant particle method used to pre-treat a skin site to facilitate improved performance from a GlucoWatch® system (Cygnus, Redwood, Calif.). This iontophoretic system is described in Glikfeld et al (1989), Pharm. Res. 6(11): 988 and in U.S. Pat. No. 5,771,890.

The interstitial fluid is the clear body fluid between cells on the top surface layer of skin. The glucose level in this fluid directly indicates the glucose level in the blood. A needleless syringe device can create diffusion micropathways into these layers of skin and give access to a small amount of interstitial fluid from which the glucose level can be measured. The present invention can be essentially free of net mass fluid transport of interstitial fluid into the interface contact element.

B. Specific Embodiments

Reference will now be made in detail to certain embodiments of the invention, an example of which is illustrated in the accompanying drawings. Wherever possible, the same reference numbers will be used throughout the drawings to refer to the same or like parts.

For the purposes of this specification, unless otherwise indicated, all numbers expressing quantities of ingredients or percentages used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Figure 1:
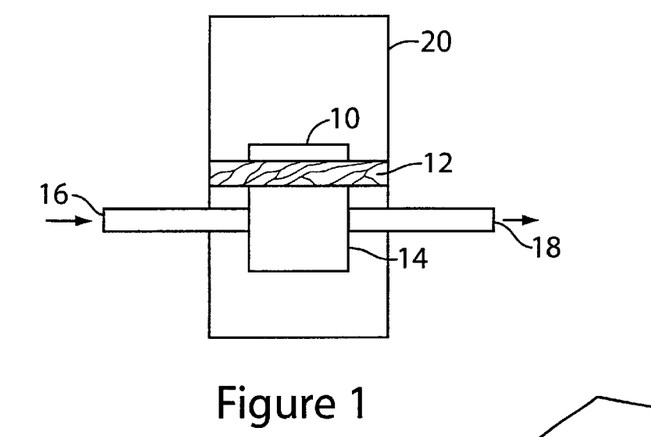
FIG. 1 illustrates an embodiment of an apparatus used to test the principles of the invention.

FIG. 1 illustrates a non-limiting embodiment of the apparatus used to test the principles of the invention. The testing apparatus (20) contains an interface contact element (10) which can be placed in contact or communication with a sensing material and detector, such as a detector incorporated in an instrument which can detect changes in analyte concentration in fluids residing in micro-pathways and on the surface of the full-thickness cadaver skin (12), thereby allowing for the detection of corresponding changes in target analyte concentration within the donor chamber (14) which is below and in contact with the cadaver skin (12). The concentration of target analyte in donor chamber (14) can be varied continuously by controlling the solution introduced into the intake (16) and the rate of flow from the exit (18) from donor chamber (14).

The term "sensor" refers to any sensing material in contact with the skin surface by means of an interface contact element. The term "interface contact element" refers to the portion of the sensor comprising any substance capable of supporting a high or unimpeded rate of diffusion of the target analyte so that the target analyte may be efficiently transported between the body fluid and the sensing material, whose volume is minimized and comprises a gel or film, largely aqueous (>95%), with viscosity and/or adhesion properties sufficient to achieve and maintain contact. In critical contrast to standard body fluid sample withdrawal methods, the interface contact element can contain a specified concentration of the target analyte (e.g., glucose) at the time of application, thereby allowing one to rapidly achieve equilibrium between the body fluid and the analyte sensing system. The pre-loaded target analyte can serve the additional function of serving as a calibrator for the analyte sensing system components at the time of initial placement over the body fluid in the micro-pathways in the skin.

Examples of interface contact elements include a hydrogel, or other hydrophilic polymer, the composition of which is predominantly water for measurement of glucose and all water-soluble target analytes, with or without surfactants or wetting agents. The interface contact element can be formulated to provide a continuous approach to equilibrium of target analyte concentration between the sensor and the body fluid. The physical properties of the interface contact element are selected to keep the sensor in close association with the skin portal. Examples of the interface contact elements include but are not limited to a 1% solution of a Carbopol® (B. F. Goodrich Co.; Cleveland, Ohio) in water, or a 4% solution of Natrosol® (Aqualon Hercules; Wilmington, Del.) in water. The interface contact element does not withdraw a sample of body fluid nor does it behave like a sink for the target analyte. The composition of the interface contact element can be selected to render it isosmotic with the body fluid such that it does not osmotically attract the body fluid. Other embodiments can comprise hydrogels including, but not limited to, poly(hydroxyethyl methacrylate) (PHEMA), poly(acrylic acid) (PAA), polyacrylamide (PAAm), poly(vinyl alcohol) (PVA), poly (methacrylic acid) (PMAA), poly(methyl methacrylate) (PMMA), poly(vinylpyrrolidone) (PVP), poly(ethylene oxide) (PEO), or poly(ethylene glycol) (PEG), avoiding polymers that can interfere with analytical methods for specific target analyte such as normal or chemically modified polysaccharides in the case of glucose measurement.

Hydrogel systems can be divided into two useful classes: microporous and macroporous, each produced by altering the quantity of water, cross-linking agent, and co-monomer present during polymerization. The diffusion rate of molecules within hydrogels can be controlled by the porosity, hydrophilicity and concentration of polymer to produce an aqueous gel with the optimal physical properties.

The interface contact element does not withdraw a sample of body fluid nor does it behave like a sink for the target analyte. The composition of the interface contact element can be selected to render it isotonic or isosmotic with the body fluid such that it does not osmotically attract mass flow of body fluid. In one embodiment, the composition can comprise a modified Ringer's-type solution to simulate interstitial fluid having a composition of NaCl (9 g/l), $CaCl_2.2H_2O$ (0.17 g/l), KCl (0.4 g/l), $NaHCO_3$ (2.1 g/l), and glucose (10 mg/l). Other embodiments can comprise simpler or more complex aqueous salt compositions with osmolality ranging from 290 mOsm/kg to 310 mOsm/kg. In one embodiment, the composition of interstitial fluid can be:

TABLE 1

| Component | mEq/l |
|---|---|
| Cations | |
| Sodium | 145 |
| Potassium | 4 |
| Calcium | 5 |
| Magnesium | 2 |
| Anions | |
| Chloride | 114 |
| Bicarbonate | 31 |
| Phosphate ($[HPO_4]^{-2}$) | 2 |
| Sulfate | 1 |
| Organic Acids | 7 |
| Proteins | 1 |

Ref: Maxwell and Kleeman (Eds.), Clinical Disorders of Fluid and Electrolyte Metabolism, McGraw-Hill, New York 1962.

The term "analyte" refers to any specific substance or component that is being detected and/or measured in a physical, chemical, biochemical, electrochemical, photochemical, spectrophotometric, polarimetric, colorimetric, or radiometric analysis. Examples include materials for blood chemistries (blood pH, $pO_2$, $pCO_2$, $Na^+$, $Ca^{++}$, $K^+$, lactic acid, glucose, and the like), for hematology (hormones, hormone releasing factors, coagulation factors, binding proteins, acylated, glycosylated, or otherwise modified proteins and the like), and immuno-diagnostics, toxins, contaminants, amino acids, enzymes, enzyme substrates or products indicating a disease state or condition, immunological substances, other markers of disease states or conditions, performance-enhancing agents, therapeutic and/or pharmacologic agents, electrolytes, physiological analytes of interest (e.g., calcium, potassium, sodium, chloride, bicarbonate ($[HCO_2]^{-2}$), glucose, urea (blood urea nitrogen), lactate, and hemoglobin), materials for DNA testing, nucleic acids, proteins, carbohydrates, lipids, electrolytes, metabolites (including but not limited to ketone bodies such as 3-hydroxybutyric acid, acetone, and acetoacetic acid), therapeutic or prophylactic drugs, gases, compounds, elements, ions, drugs of recreation and/or abuse, anabolic, catabolic or reproductive hormones, anticonvulsant drugs, antipsychotic drugs, alcohol, cocaine, cannabinoids, opiates, stimulants, depressants, and their metabolites, degradation products and/or conjugates. A detectable signal can be obtained, either directly or indirectly, from such a material. Moreover, also included are any chemicals that have a physiological action, for example a drug or pharmacological agent such that when administered to an organism (human or animal), induces a desired pharmacological and/or physiological effect by local and/or systemic action. The term "target" analyte refers to the analyte of interest.

Figure 2:
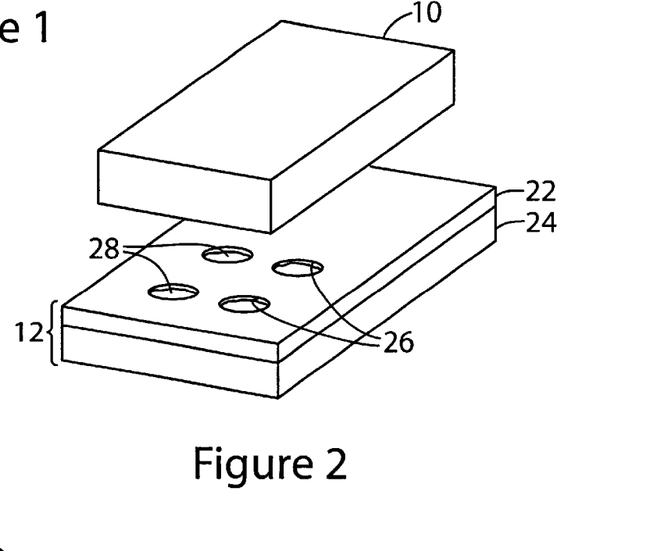
FIG. 2 illustrates an embodiment of an interface contact element positioned on the skin.

FIG. 2 illustrates a non-limiting embodiment of the interface contact element portion of a sensor produced according to the present invention. The interface contact element (10) is shown positioned over the skin (12). The skin (12) tissue comprises multiple layers, including the stratum corneum (22) (the outermost layer of the skin), the epidermis (24), and underlying dermis (not shown). The skin (12) may contain micro-pathways (26) that transit the stratum corneum (22) and enter the epidermis (24) thereby providing micro-pathways for the body fluid (28). A variety of methods are known to expose the body fluid by creating micro-pathways. The term "micro-pathways" refers to microscopic perforations and/or channels in the skin caused by pressure (water or particle injection), mechanical (micro lancets), electrical (thermal ablation, electro-poration, or electroosmosis), optical (laser ablation), and chemical methods or a combination thereof. The term "body fluid" refers to sub-epidermal fluids including, but not limited to interstitial fluid, blood, lymph, sweat, or any other body fluid accessible at the surface of the skin.

Figure 3:
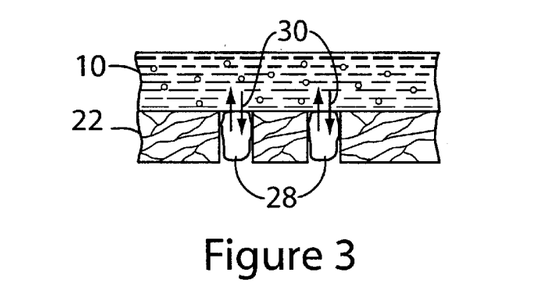
FIG. 3 illustrates an embodiment of the interface between the interface contact element and the body fluid.

FIG. 3 illustrates a non-limiting embodiment of the interface between the interface contact element and the body fluid. The interface contact element (10) contacts the body fluid (28) through the breaks in the stratum corneum (22). Once the stratum corneum (22) has been perforated with micro-pathways, as discussed above, the diffusional barrier to analyte transport can be reduced or eliminated. This facilitates diffusion (30) from the interface contact element (10) to the body fluid (28), and vice versa, both essentially free of net mass fluid transport of interface contact element (10) or body fluid (28). The target analyte, or any other substance diffuses between the interface contact element (10) and body fluid (28) with essentially no net mass flow of interface contact element (10) into the body fluid (28), and essentially no net mass flow of body fluid (28) into interface contact element (10).

The term "diffusion" refers to the flux across the interface between the body fluid and the interface contact element along a concentration gradient. Such diffusion includes transport of the target analyte to maintain equilibrium between the body fluid and the interface contact element. When the concentration of analyte is greater in the body, analyte diffusion would be toward the interface contact element. When the concentration of analyte is greater in the interface contact element, analyte diffusion would be toward the body. In addition, net diffusion of analyte from the interface contact element to the body fluid will occur when the concentration of analyte in the body decreases with respect to the previous measurement. Diffusion, however, is not limited to the target analyte. Certain means of measurement, for example those employing enzymatic electrochemical approaches, can generate natural byproducts by oxidation or reduction of the analyte such as gluconic acid or gluconolactone in the case of glucose. Such byproducts can diffuse from the sensing material into the interface contact element, and in turn diffuse into the body fluid. An interface that facilitates the establishment and maintenance of an equilibrium concentration of analyte by diffusion is desired to permit a virtually continuous measurement during long-term monitoring without saturating the interface contact element with byproducts or even the target analyte.

In one embodiment, the interface contact element comprises a specific concentration of the target analyte within the normal range of analyte concentration in the body fluid so that the interface contact element can reach equilibrium more rapidly with diffusion of less of the target analyte. This embodiment can avoid calibration by a blood fingerstick. Calibration is intended to compensate for differences in manufactured sensors. The interface contact element can be packaged separately from the sensing material (e.g., the enzymatic electrode). The specific concentration can be a precise amount of target analyte whose quality can be controlled with very sensitive and accurate methods.

In one embodiment, the target analyte can be glucose and the body fluid can be interstitial fluid. As opposed to other glucose monitoring composition and methods that withdraw an amount of body fluid, the present invention can contain a specified concentration of glucose at the time of application to the skin and creation of the interface with the interstitial fluid. Hence, equilibrium can more rapidly be achieved between the body fluid and the interface contact element. The specific concentration of glucose can serve the additional function of calibrating the sensing material and detector at the time of initial placement over interstitial fluid made accessible through the micro-pathways.

The specific concentration of glucose can be chosen to be at or near the average level measured by the sensor in healthy patients to decrease the time that elapses for diffusion to drive the glucose concentration of the interface contact element to equilibrium with the interstitial fluid glucose concentration. Alternatively, the specific concentration of glucose can be chosen to be at or near the average level measured by the sensor in diabetic patients. Alternatively, the specific concentration of glucose can be chosen to be a low value to track the increase in glucose concentration in the interface contact element over time (e.g., using built-in logic in the instrument) to assess either the quality of the sensing material through initial measurements, or the micro-pathways through the rate of increase to plateau. Hence, the instrument can monitor the viability of the sensing material and the success of creating the micro-pathways.

The range of blood glucose concentration for a normal, healthy person can be from 60–120 mg/dl to 80–120 mg/dl. The blood glucose level for a diabetic person can range from greater than 120 mg/dl to greater than 200 mg/dl for hyperglycemic episodes; from less than 60 mg/dl to less than 80 mg/dl for hypoglycemic episodes where there is excess insulin either through administration (e.g., oral, pulmonary or injection) or pancreatic secretion; and as high as 400–500 mg/dl for uncontrolled diabetes. L. P. Krall, et al., *Joslin Diabetes Manual*, (12$^{th}$ ed., Lea & Febiger 1989). For most diabetics, the blood glucose concentration is generally maintained higher than 120 mg/dl due to the fact that imperfect control at lower levels holds the risk of hypoglycemic shock, coma, and even death.

In one embodiment, the interface contact element comprises a specific concentration of 0.05–0.5% of glucose by weight of interface contact element. The specific concentration can be chosen to reduce or optimize the amount of glucose that must diffuse from the body to reach the equilibrium at the interface between the interface contact element and the interstitial fluid when placed on the micropathway perforated skin. This specific concentration can be accurately measured at the time of manufacture of the interface contact element. In another embodiment, the specific concentration of glucose can be chosen to approach glucose levels in the interstitial fluid and be equivalent to the ranges of glucose in the blood for healthy or diabetic patients, such as the ranges discussed above. Such equivalencies of glucose concentration in the blood to glucose concentration in the interstitial fluid are known to one skilled in the art. The term "equivalent" refers to correlations between the concentrations of analyte in the blood and concentrations of analyte in the body fluid, either particular to the individual or generalized to a particular patient group. In another embodiment, the interface contact element comprises a specific concentration of 0.08–0.3% of glucose by weight of interface contact element. This specific concentration can be chosen to reduce or optimize the amount of glucose that must diffuse from the body to reach the equilibrium at the interface between the interface contact element and the interstitial fluid when placed on the micropathway perforated skin. In another embodiment, a low specific concentration of glucose in the interface contact element can be chosen so that the approach to equilibrium is always by glucose diffusion from the interstitial fluid. In another embodiment, the interface contact element comprises a specific concentration of 0.1% glucose by weight of interface contact element. In another embodiment, the specific concentration of glucose can be used to calibrate the sensing material. In this embodiment, the glucose diffuses from the interstitial fluid to the interface contact element in the case of a hyperglycemic state, and from the interface contact element to the interstitial fluid in the case of a hypoglycemic state.

To maintain specific concentration of glucose in the interface contact element it can be stored at pH 5 to 7, and sterilized using radiation and/or kept sterile by means of aseptic manufacturing techniques. The interface contact element can be packaged separately from the sensing material. The interface contact element with a specific concentration of glucose can lose its effectiveness if stored with a sensing material that reacts with the glucose. In one embodiment, the interface contact element contact can be kept separate in isolation packaging from the sensing material until immediately prior to placement. The interface contact element and sensing material, either sterile or at a very low bioburden, can be joined by a package element such as a roller immediately prior to placement or joined dry in manufacture and rehydrated as a unit prior to placement by means of a package element such as a water or aqueous buffer compartment.

In one embodiment, a packaging container can have multiple compartments, one for the interface contact element, and another for the sensing material with the patch. The compartments of the plastic packaging can be separated by a sheet separating the interface contact element and the sensing material. The packaging can be sealed in the packaging container adapted to leave the ends for the sheet free such that the sheet can be slidably removed from the container. The sheet can thus be removed just prior to use, allowing the interface contact element to come into contact with the sensing material and patch, after which step, the container can be opened and the patch with sensing material and interface contact element applied on the skin. Such packaging prevents the interface contact element with a specific concentration of glucose from losing its effectiveness by coming into to contact with the sensing material, which reacts with the glucose, prior to forming the interface with the interstitial fluid. Such packaging further allows the enzymatic electrosensing element to be stored in an essentially dry form until use, at which time it may be hydrated to an active state by water in the interface contact element or in another compartment of the package.

In another embodiment, the interface contact element comprises a specific concentration of inorganic salts (e.g., the ions of sodium, potassium, calcium, magnesium, chloride, bicarbonate, phosphate, sulfate, and other salts found in body fluid; see Table 1) such that the interface contact element can be isosmotic with the body fluid, thereby allowing the sensor to reach equilibrium through diffusion of target analyte without mass fluid flow. Any significant imbalance of salt concentration between the interface contact element and the interstitial fluid can establish an osmotic potential that would cause water to be drawn into or away from the interface contact element. Depending upon the amount of fluid flow, this can adversely affect either the properties of the interface contact element or the interstitial fluid balance in the underlying tissue. Isosmolality can be established by an approximation of the multi-salt composition of interstitial fluid (e.g., Table 1) or by the selection of concentration of few salts or even a single salt to achieve osmolality of 290–310 mOsm/l. Such specific concentrations of analytes in the interface contact element can be preserved prior to application to the interstitial fluid by a packaging container with multiple compartments similar to the one discussed above.

The term "equilibrium" refers to the phenomenon in which diffusion has equalized the concentration of analyte on either side of the interface such that there is essentially no concentration gradient. Diffusion of analyte between the body fluid and the interface contact element allows approach to an equilibrium or steady state. When concentrations of analyte change in the body, a timely dynamic change in the equilibrium enables continuous monitoring of the analyte concentration. The physical measurement of the analyte concentration can avoid transforming a significant amount of the analyte such that the reduced amount of analyte in the interface contact element does not render it a sink for the analyte. In the situation that the interface contact element becomes a sink, continuous monitoring of analyte concentration can measure the rate of diffusion instead of concentration in the event that the time to reach equilibrium between the interface contact element and the body fluid is not sufficient.

The term "mass fluid transport" refers to the movement of fluids, such as body fluid or interface contact element. This fluid transport is used to distinguish over analyte transport across the interface between the body fluid and the sensor's interface contact element. The mass transport aspect refers to the physical movement of the fluid as opposed to the movement of energy, or solutes between the body fluid and the interface contact element. The modifier of "net" mass fluid transport refers to the sum of transport back and forth across the interface. Accordingly, transport in one direction across the interface is negated by transport in the opposite direction such that the net transport can be zero.

The term "essentially free" refers to an insubstantial amount of mass fluid transport between the body fluid and interface contact element (i.e., a volume less than the volume of the interface contact element or a small fraction of it). The volume of the interface contact element can be on the order of 5 or greater micro-liters. The net volume of interstitial fluid flux throughout the life of the interface contact element (i.e., 10–20 hours) should be less than the volume of the interface contact element.

The term "instrument" refers to a device comprising a detector configured to contact the sensor (e.g., the sensor can be incorporated into a patch comprising the interface contact element and sensing material) and determine the presence and/or concentration of a target analyte by means of a signal from a sensor based upon at least one analytical method. The term "analytical method" refers to electrochemical (e.g., amperometric or coulometric), direct or reflective spectroscopic (e.g., fluorescent or chemiluminescent), biological (e.g., enzymatic), chemical, optical, electrical, mechanical (e.g., measuring gel expansion via piezoelectric means) methods known in the art for sensing the presence or concentration of analytes in solution. The term "sensing material" refers to any composition that enables the analytical method to be performed.

The instrument can take many forms that can facilitate the appropriate measurement interval during continuous monitoring or convenient intermittent measurement including, but not limited to, a pen-style reading device or a watch-style reading device. The instrument contains a detector which may take readings from the sensor intermittently when the instrument contacts the sensor or when a reading is triggered by a solid-state logic and/or recording circuit in the instrument. Such intermittent measurements can be predetermined so that the time interval between measurements is sufficiently short that the measurement approaches a continuous reading. The instrument can be capable of calculating trends using a microprocessor to anticipate conditions, such as dangerous nocturnal hypoglycemic events (especially in children). The sensor can be configured into a patch that contacts the interface contact element. A non-limiting embodiment of the sensor patch houses an electronic circuit with an occlusive backing and a peripheral adhesive. The electronic circuit contains terminals on the outside surface of the patch assembly to access an electrode on the detector. The electrode terminals can be designed so as not to require the precise positioning of the instrument on the patch to ensure proper contact between the sensor and detector, such as circular concentric contact terminals on the outer surface of the patch and staggered terminal contacts on the detector or vice versa. Alternatively, physical features of the patch and detector such as interlocking or complementary detents can guide the elements into proper register for contact.

EXAMPLE 1

This example shows the relationship between analyte concentration within an experimental system and the signal obtained from analyte measurement using an interface contact element that is in contact with the external surface of that system. A modified Franz cell testing apparatus was used to model skin tissue containing glucose analyte in interstitial fluid. The donor part of the bottom of the Franz cell was filled with a liquid that approximated interstitial fluid, and various amounts of glucose were added to the liquid. Human cadaver skin was placed over the top of the Franz cell to provide the external monitoring surface.

More particularly, interstitial fluid is the clear body fluid found between cells in the top surface layers of skin, i.e., the dermis and epidermis. Dermal interstitial fluid glucose concentrations have been shown to be directly proportional to blood glucose concentrations (*J Lab Clin Med.*1997; 130:436–441) thus measurement of the glucose level in this fluid directly indicates the glucose level in blood. A needle-less syringe device can create diffusion micro-pathways to the epidermis. For this in vitro test, phosphate buffered saline was used as a surrogate for interstitial fluid. Using the modified Franz cell testing apparatus (20) illustrated in FIG. 1, in which concentrations in the donor chamber (14) can be varied through the intake (16) and exit (18), glucose was detected at the surface of full-thickness cadaver skin (12) having diffusion micro-pathways created by injection of powdered lactose monohydrate, NF, grade from Amresco, Inc. (Solon, Ohio).

The lactose powder was sieved to 38–53 microns using U.S. Standard Sieves (Chicago, Ill.). D-(+) glucose was obtained from Sigma Chemical Co. (St. Louis, Mo.). Human cadaver skin supplied from the New York Firefighter Skin Bank (New York, N.Y.), was pretreated with 80% balanced salt solution, 10% calf serum and 10% glycerol and frozen at the skin bank. The skin was used as supplied after thawing 1–2 hours at room temperature. The skin was placed over the modified Franz cell or flow-through diffusion cell.

After a few hours for equilibration, 1 mg of lactose particles of 38–53 micron diameter were filled into tri-laminate particle cassettes having 10 micron polycarbonate rupturable membranes, and the lactose particles were then injected into the skin tissue using a $CO_2$-powered multi-shot particle injection device (PowderChek Diagnostics, Inc., Fremont, Calif.) fitted with a supersonic nozzle. Device pressure for particle administration was equivalent to 10 bar of $CO_2$ gas. Five microliters of 1% aqueous hydrogel (Carbopol®, B. F. Goodrich Co., Cleveland, Ohio) was applied to the surface of the injected skin as the interface contact element. An electrochemical sensor/detector was used to generate an output signal in nanoamperes by continuous contact with a custom fabricated sensor/signal reading device.

The concentration of the glucose solution was varied between 0–400 mg/dl. The temperature of the glucose solution was maintained at 32 degrees Celsius during the experiments. Three different samples of human cadaver skin, each having a thickness of 200–300 µm, were used in the study. The results of the study, wherein various glucose concentrations were detected by a current reading from the electrochemical sensor, are shown herein below in Table 2.

TABLE 2

| Glucose concentration (mg/dl) | Average output signal (nA) |
|---|---|
| 0 | 44 ± 16 |
| 100 | 61 ± 6 |

TABLE 2-continued

| Glucose concentration (mg/dl) | Average output signal (nA) |
|---|---|
| 200 | 65 ± 13 |
| 400 | 80 ± 12 |

As can be seen, the average output signal readings obtained from the surface of the skin increased with the increase of glucose concentration within the Franz cell, demonstrating that analyte concentration within a model skin tissue system can be monitored by repeatable signal readings obtained by contacting a sensor with the exterior surface of the skin.

EXAMPLE 2

The purpose of the following example was to demonstrate the ability of a sensor constructed according to the present invention to track analyte concentration within a dynamic test system. The sensor was also assessed for its ability to detect and provide analyte concentration measurements from a changing system.

The materials and methods used in Example 1 above were employed in this Example 2; however, the concentration of the glucose analyte within the modified Franz cell (within the donor chamber) was changed over approximately ten minute intervals from 0 mg/dl to approximately 400 mg/dl and then to 0 mg/dl. The cycle was repeated once the experimental value reached the actual concentration. An electrochemical sensor/detector was used to generate an output signal in nanoamperes detected by continuous contact with a custom fabricated signal reading device. The response of the sensor to the change in glucose concentration was monitored over time and translated into glucose concentrations. The results are shown in FIG. 4.

Figure 4:
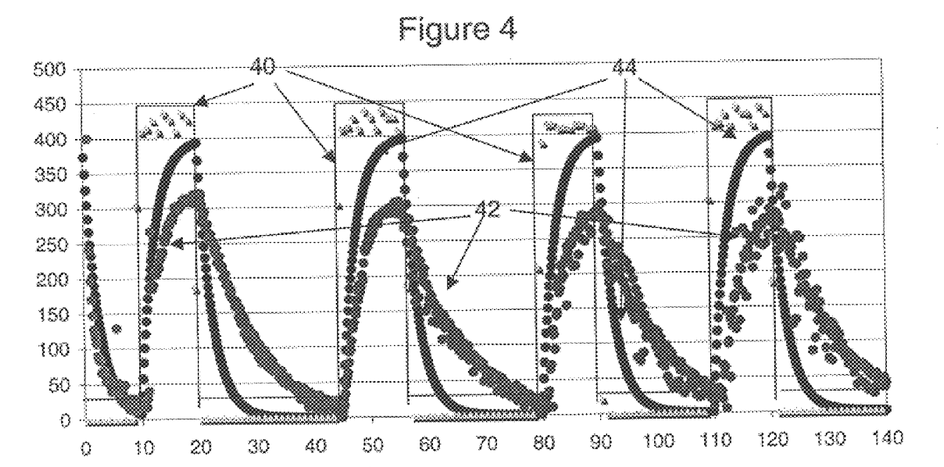
FIG. 4 illustrates a graph of continuous glucose monitoring showing the concentration of glucose versus time for actual glucose concentration, the experimental value, and the theoretical diffusion value.

Referring now to FIG. 4, the vertical axis represents concentration of glucose in mg/dl and the horizontal axis represents time in minutes. The actual glucose concentration (indicated as element 40 in FIG. 4) within the donor chamber was varied over time. The experimental glucose concentration (indicated as element 42 in FIG. 4) detected by the sensor at the skin surface shows that the measured analyte concentration lagged behind the actual glucose concentration (40) within the donor chamber by the rate of diffusion. The theoretical glucose concentration (indicated as element 44 in FIG. 4) expected to be found at the skin surface was calculated based on the following equation:

$$M = DSK(C_d - C_r)/h*t$$

wherein (M) is the theoretical concentration of glucose at the skin surface; (D) is the glucose diffusion coefficient (across the skin tissue) in $cm^2$/second; (K) is the glucose partition coefficient in the epidermal layer; (S) is the diffusion area in millimeters; ($C_d$) is the glucose concentration in the donor chamber in mg/dl; ($C_r$) is the glucose concentration in the receiver or interface contact element in mg/dl; (h) is the thickness of the skin tissue in microns; and (t) is time in seconds. The value for the glucose diffusion coefficient was assumed to be the value of diffusion of glucose in 100% water, i.e., $6.8 \times 10^{-6}$ $cm^2$/second. The calculation assumed that the perforated skin does not have any barrier properties.

During the study, the concentration of the glucose analyte within the interface contact element (10) was initially fixed at 400 mg/dl. As the glucose present in the interface contact element and the glucose within the test chamber approached equilibrium (the glucose diffused from the interface contact element, through the cadaver skin into the donor chamber, and was removed through the outlet), the experimental glucose concentration (42) detected at the skin surface approached 0 mg/dl. Next, the actual glucose concentration (40) within the donor chamber was increased to 400 mg/dl. The experimental glucose concentration (42) measured at the skin surface tracked the actual glucose concentration (40) within the donor chamber as the glucose diffused from donor chamber, through the skin tissue and into the interface contact element. The experimental glucose concentration (42) detected at the surface of the skin also tracked the theoretical glucose concentration (44). These results show that the glucose concentration in the interface contact element reflects positive and negative fluctuations in glucose concentrations in body fluid underlying the skin into which micro-pathways have been made. This is achieved by diffusing glucose from the interface contact element through the skin into the underlying body fluid and diffusing glucose from the body fluid through the skin into the interface contact element. This diffusion through the skin can occur within a relatively short period of time.

EXAMPLE 3

The following study is carried out to assess continuous monitoring of analyte concentration using the methods and apparatus of the present invention. More particularly, in vivo tests are performed on diabetic patients or healthy volunteers using intravenous lines with pumps to deliver insulin and glucose, and an indwelling sensor catheter (Biostator, Life Science Instruments, Elkhart, Ind.) to measure real-time glucose concentration in the blood. In the healthy volunteers, a low dose intravenous infusion of somatostatin is used to suppress the body's natural insulin release in response to glucose administration (Diabetes Tech. & Ther., 2000; 2:211–220). The interface contact element and sensor are applied to an abdominal site (or other suitable target surface) that is pretreated to create micro-pathways (e.g., by particle injection). The subjects do not have a history of skin problems (i.e., dermatitis, eczema, psoriasis, or keloid formation). The subjects are subjected to several patterns of blood glucose concentrations via the intravenous infusion. Blood glucose is monitored by the indwelling sensor, the glucose concentration in interstitial fluid is measured by an interface contact element and sensor constructed according to the present invention, and these readings are cross-referenced with the readings from an intradermal continuous glucose monitoring system (CGMS™, MiniMed, Northridge, Calif.) which measures interstitial fluid glucose concentration.

As a result of the study, it is further illustrated that interstitial fluid accessed continuously through micro-pathways (e.g., those created by particle injection) is a representative sample of interstitial fluid. In addition, it is seen that there is no significant diffusional boundary or barrier to continuous access of interstitial fluid through the micro-pathways, and that the micro-pathways remain viable for an extended period of time. Furthermore, the ratio of interstitial fluid glucose concentration and blood glucose concentration is constant over time such that there is no significant time lag or damping effects between blood glucose concentration and interstitial fluid glucose concentration and, finally, there is neither significant subject-to-subject variation nor site-to-site variation seen in the study.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A sensor for measuring or detecting a target analyte, said sensor comprising an interface contact element that is capable of establishing an interface with a quantity of body fluid containing or suspected of containing the analyte, wherein said interface contact element is adapted to diffusion of the analyte essentially free of net mass fluid transport across said interface, characterized in that said interface contact element comprises an aqueous component that is isosmotic with the body fluid.

2. The sensor of claim 1, wherein said interface contact element further comprises a specific concentration of an inorganic salt also found in the body fluid.

3. The sensor of claim 1 further comprising a sensing material that is capable of specifically detecting the presence, or both the presence and amount of analyte present in the interface contact element.

4. The sensor of claim 1, wherein the interface contact element is adapted for placement upon a target skin surface.

5. A sensor for measuring or detecting a target analyte, said sensor comprising an interface contact element that is capable of establishing an interface with a quantity of body fluid containing or suspected of containing the analyte, wherein said interface contact element is adapted to diffusion of the analyte essentially free of net mass fluid transport across said interface, characterized in that said interface contact element comprises a specific concentration of the target analyte prior to being interfaced with the quantity of body fluid.

6. The sensor of claim 5, wherein the target analyte is glucose.

7. The sensor of claim 6, wherein the interface contact element comprises from 0.05 to 0.5% glucose by weight of said interface contact element.

8. The sensor of claim 7 wherein the interface contact element comprises from 0.08% to 0.3% glucose by weight of said interface contact element.

9. The sensor of claim 7 wherein the interface contact element comprises 0.1% glucose by weight of said interface contact element.

10. The sensor of claim 6, wherein the interface contact element comprises an amount of glucose equivalent to from 60 to 120 mg/dl glucose in blood.

11. The sensor of claim 6, wherein the interface contact element comprises an amount of glucose equivalent to less than 60 mg/dl glucose in blood.

12. The sensor of claim 6, wherein the interface contact element comprises an amount of glucose equivalent to greater than 120 mg/dl glucose in blood.

13. The sensor of claim 5, wherein said interface contact element comprises an aqueous component that is isosmotic with the body fluid.

14. The sensor of claim 13, wherein said interface contact element further comprises a specific concentration of an inorganic salt also found in the body fluid.

15. The sensor of claim 5 further comprising a sensing material that is capable of specifically detecting the presence, or both the presence and amount of analyte present in the interface contact element.

16. The sensor of claim 5, wherein the interface contact element is adapted for placement upon a target skin surface.

17. A method for measuring or detecting a target analyte in a quantity of body fluid containing or suspected of containing the analyte, said method comprising:

(a) exposing a quantity of body fluid through a micropathway created in a tissue surface;

(b) providing an interface contact element;

(c) establishing an interface at the tissue surface between the body fluid exposed through the micropathway and the interface contact element;

(d) allowing said analyte to diffuse across said interface into the interface contact element, wherein diffusion of the analyte occurs essentially free of net mass fluid transport across said interface; and (e) measuring or detecting target analyte that has diffused into the interface contact element.

18. The method of claim 17, wherein diffusion of the target analyte into the interface contact element is sufficient to approach continuous equilibrium of analyte concentration between the interface contact element and the quantity of body fluid.

19. The method of claim 17, wherein the micro-pathway is created in a skin tissue surface.

20. The method of claim 19, wherein the micro-pathway is created through the stratum corneum layer of the skin tissue.

21. The method of claim 17, wherein the micro-pathway is created using a particle injection device.

22. The method of claim 17, wherein the interface contact element is adapted to diffusion of the analyte essentially free of net mass fluid transport across said interface.

23. The method of claim 22, wherein the interface contact element comprises an aqueous component that is isosmotic with the body fluid.

24. The method of claim 22, wherein the interface contact element comprises a specific concentration of the target analyte prior to being interfaced with the quantity of body fluid.

25. The method of claim 17, wherein the concentration of the target analyte in the interface contact element is measured between predetermined time intervals.

26. The method of claim 17, wherein the concentration of the target analyte in the interface contact element is measured continuously.

27. The method of claim 17 wherein the body fluid comprises interstitial fluid.

28. The method of claim 17 wherein the target analyte is glucose.

* * * * *